United States Patent [19]

Lombardino

[11] 4,309,427

[45] Jan. 5, 1982

[54] BENZOTHIAZINE DIOXIDE DERIVATIVES

[75] Inventor: Joseph G. Lombardino, Niantic, Conn.

[73] Assignee: Pfizer Inc., New York, N.Y.

[21] Appl. No.: 225,162

[22] Filed: Jan. 15, 1981

[51] Int. Cl.³ .................... C07D 279/02; A61K 31/54
[52] U.S. Cl. ........................................ 424/246; 544/49
[58] Field of Search ........................... 544/49; 424/246

[56] References Cited

U.S. PATENT DOCUMENTS 3,591,584  7/1971  Lombardino .................... 544/49
3,925,371 11/1975  Rasmussen ..................... 544/49
4,116,964  9/1978  Zinnes et al. .................. 544/49

OTHER PUBLICATIONS

J. G. Lombardino et al., "Potent Antiinflammatory N-Heterocyclic3-Carboxamides of 4-Hydroxy-2-methyl-2H-1,2-benzothiazine 1,1-Dioxide", *Journal of Medicinal Chemistry, vol. 16, No. 5, p. 493, (1973).*

Primary Examiner—John M. Ford

Attorney, Agent, or Firm—Francis X. Murphy; Charles J. Knuth; Peter C. Richardson

[57] ABSTRACT

Certain novel derivatives of N-(2-pyridyl)-2-methyl-4-hydroxy-2H-1,2-benzothiazine-3-carboxamide 1,1-dioxide have been prepared, including N-(2-pyridyl)-2-methyl-4-acetoxy-2H-1,2-benzothiazine-3-carboxamide 1,1-dioxide, N-(2-pyridyl)-2-methyl-4-(n-butyryloxy)-2H-1,2-benzothiazine-3-carboxamide 1,1-dioxide, N-(6-methyl-2-pyridyl)-2-methyl-4-acetoxy-2H-1,2-benzothiazine-3-carboxamide 1,1-dioxide, N-(2-pyridyl)-2-methyl-4-benzoyloxy-2H-1,2-benzothiazine-3-carboxamide 1,1-dioxide, N-(6-methyl-2-pyridyl)-2-methyl-4-benzoyloxy-2H-1,2-benzothiazine-3-carboxamide 1,1-dioxide, N-(2-pyridyl)-2-methyl-4-methanesulfonyloxy-2H-1,2-benzothiazine-3-carboxamide 1,1-dioxide and N-(6-methyl-2-pyridyl)-2-methyl-4-methanesulfonyloxy-2H-1,2-benzothiazine-3-carboxamide 1,1-dioxide. All these compounds are useful in therapy as non-steroidal anti-inflammatory agents, especially when administered by the topical route of administration. Methods for preparing these compounds from known starting materials are provided.

14 Claims, No Drawings

BENZOTHIAZINE DIOXIDE DERIVATIVES

BACKGROUND OF THE INVENTION

This invention relates to new and useful benzothiazine dioxide derivatives. More particularly, it is concerned with a novel series of acyl derivatives of N-(2-pyridyl)-2-methyl-4-hydroxy-2H-1,2-benzothiazine-3-carboxamide 1,1-dioxide and N-(6-methyl-2-pyridyl)-2-methyl-4-hydroxy-2H-1,2-benzothiazine-3-carboxamide 1,1-dioxide, respectively, which are of especial value in view of their unique chemotherapeutic properties.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including a new agent known as piroxicam. The latter substance is a member of a class of anti-inflammatory 4-hydroxy-2H-1,2-benzothiazine-3-carboxamide, 1,1-dioxides described and claimed in U.S. Pat. No. 3,591,584. However, in the continuing search for improved anti-inflammatory agents, there is a need for agents adapted for topical administration.

SUMMARY OF THE INVENTION

In accordance with the present invention, it has now been found that certain novel acyl derivatives of N-(2-pyridyl)-2-methyl-4-hydroxy-2H-1,2-benzothiazine-3-carboxamide 1,1-dioxide and N-(6-methyl-2-pyridyl)-2-methyl-4-hydroxy-2H-1,2-benzothiazine-3-carboxamide 1,1-dioxide, respectively, are useful as non-steroidal therapeutic agents for alleviating various inflammatory conditions, including those of the skin. The novel compounds of this invention are derivatives of N-(2-pyridyl)-2-methyl-4-hydroxy-2H-1,2-benzothiazine-3-carboxamide 1,1-dioxide having the formula:

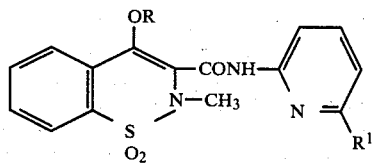

wherein R is selected from the group consisting of alkanoyl having from two to nine carbon atoms, benzoyl, toluoyl, thenoyl, furoyl, lower alkanesulfonyl and benzenesulfonyl, and $R^1$ is hydrogen or methyl. These compounds are useful in alleviating inflammatory conditions, especially when given by the topical route.

Typical and preferred compounds of the invention include N-(2-pyridyl)-2-methyl-4-acetoxy-2H-1,2-benzothiazine-3-carboxamide 1,1-dioxide, N-(2-pyridyl)-2-methyl-4-(n-butyryloxy)-2H-1,2-benzothiazine-3-carboxamide 1,1-dioxide, N-(6-methyl-2-pyridyl)-2-methyl-4-acetoxy-2H-1,2-benzothiazine-3-carboxamide 1,1-dioxide, N-(2-pyridyl)-2-methyl-4-benzoyloxy-2H-1,2-benzothiazine-3-carboxamide 1,1-dioxide, N-(6-methyl-2-pyridyl)-2-methyl-4-benzoyloxy-2H-1,2-benzothiazine-3-carboxamide 1,1-dioxide, N-(2-pyridyl)-2-methyl-4-methanesulfonyloxy-2H-1,2-benzothiazine-3-carboxamide 1,1-dioxide and N-(6-methyl-2-pyridyl)-2-methyl-4-methanesulfonyloxy-2H-1,2-benzothiazine-3-carboxamide 1,1-dioxide, respectively. These compounds are especially effective in treating various inflammatory conditions of the skin when administered by the topical route.

DETAILED DESCRIPTION OF THE INVENTION

In the process for preparing the novel compounds of this invention, N-(2-pyridyl)-2-methyl-4-hydroxy-2H-1,2-benzothiazine-3-carboxamide 1,1-dioxide or N-(6-methyl-2-pyridyl)-4-hydroxy-2H-1,2-benzothiazine-3-carboxamide 1,1-dioxide is treated with at least an equivalent amount in moles of an acyl halide of the formula RX where R is as previously defined and X is either chlorine or bromine. This reaction is normally carried out in a reaction-inert organic solvent under substantially anhydrous conditions in the presence of a suitable amount of an appropriate standard basic agent. In general, the reaction is conducted at a temperature of from about 0° C. up to about 50° C. for a period of about one-half to about 64 hours, although it is usually most convenient to conduct the reaction at room temperature. Although any inert organic solvent may be used, it is generally most desirable to employ such solvents as aromatic hydrocarbons, halogenated lower hydrocarbons, lower alkyl ketones, lower alkyl esters of lower alkane hydrocarbon carboxylic acids, lower dialkyl ethers, dioxane and tetrahydrofuran. Preferred aromatic hydrocarbons include benzene, toluene and xylene; preferred halogenated lower hydrocarbons include methylene chloride, chloroform, ethylene dichloride and s-tetrachlorethane; preferred lower alkyl ketones include acetone, methyl ethyl ketone and methyl isobutyl ketone; preferred lower alkyl esters include methyl acetate, ethyl acetate, isopropyl acetate, methyl propionate and ethyl propionate; while preferred lower dialkyl ethers include diethyl ether, diisopropyl ether and di-n-butyl ether. Appropriate standard basic agents for use in this process include the alkali metal and alkaline-earth metal oxides, bicarbonates and carbonates, such as magnesium oxide, sodium bicarbonate, sodium carbonate and magnesium carbonate, as well as tertiary amines such as triethylamine, N,N-dimethylaniline and pyridine. It should be noted that the standard basic agent employed must be present in sufficient amount to neutralize the liberated hydrogen halide formed in the reaction. Triethylamine is most preferred because it can easily be removed from the reaction mixture in the form of an insoluble solid hydrohalide precipitate.

Alternatively, it is also possible to prepare compounds of the invention where R is other than lower alkanesulfonyl or benzenesulfonyl by contacting the appropriate N-(2-pyridyl)-2-methyl-4-hydroxy-2H-1,2-benzothiazine-3-carboxamide 1,1-dioxide starting compound under substantially anhydrous conditions with an acylating agent selected from the class consisting of the corresponding carboxylic acid anhydrides having the formula $(RCO)_2O$, where R is as previously defined except for the above proviso. This reaction is normally carried out in the presence of an organic base, such as a tertiary amine, as catalyst (although this is not absolutely necessary) at a temperature of from about 20° C. up to about 120° C. for a period of about one-half to about 24 hours. The molar ratio of acylating agent to the 4-hydroxy starting material should be from about 1:1 to about 5:1, while the amount of tertiary amine employed is normally about 25 to 150% by weight of the aforesaid acylating agent (the tertiary amine may be used as the reaction solvent by merely employing an excess of same). Although it is quite possible and even, in some instances, highly desirable to carry out the reaction in the absence of a solvent, there may be times when the use of a suitable reaction-inert organic solvent is clearly indicated, e.g., if and when the acylating agent employed is a solid compound. Suitable solvents include neutral, inert anhydrous organic solvents, such as acetone, methyl ethyl ketone, benzene, toluene, xylene, dioxane, tetrahydrofuran, methylene chloride, chloroform, ethylene dichloride, tetrachlorethane, methyl acetate, ethyl acetate, isopropyl acetate, methyl propionate, ethyl propionate, diethyl ether, diisopropyl ether, di-n-propyl ether and the like. However, as previously indicated, the reaction is ordinarily conducted in the absence of such a solvent by merely employing an excess of the acylating agent if the latter is a liquid. Similarly, an excess of the tertiary amine reagent may also serve as a solvent. Preferred tertiary amines for use as solvents and/or as catalytic reagents in this reaction include triethylamine, dimethylaniline, pyridine, picoline, lutidene, collidine and quinoline.

The starting materials required for preparing the novel N-(2-pyridyl)-2-methyl-4-acyloxy-2H-1,2-benzothiazine-3-carboxamide 1,1-dioxide derivatives of this invention are both known compounds. For instance, N-(2-pyridyl)-2-methyl-4-hydroxy-2H-1,2-benzothiazine-3-carboxamide 1,1-dioxide (piroxicam) and N-(6-methyl-2-pyridyl)-2-methyl-4-hydroxy-2H-1,2-benzothiazine-3-carboxamide 1,1-dioxide are both fully described in U.S. Pat. No. 3,591,584 to J. G. Lombardino, as well as in the paper to J. G. Lombardino et al., appearing in the *Journal of Medicinal Chemistry*, Vol. 16, p. 493 (1973), including their synthesis from readily available organic materials. The acylating agents employed to prepare the novel derivatives of this invention are all commercially available materials.

The N-(2-pyridyl)-2-methyl-4-acyloxy-2H-1,2-benzothiazine-3-carboxamide 1,1-dioxide compounds of the present invention are all readily adapted to therapeutic use as anti-inflammatory agents. For instance, N-(2-pyridyl)-2-methyl-4-(n-butyryloxy)-2H-1,2-benzothiazine-3-carboxamide 1,1-dioxide, a typical and preferred agent of the present invention, exhibits remarkable activity in the standard carrageenin-induced rat food edema test [described by C. A. Winter et al., *Proc. Soc. Exp. Biol. Med.*, Vol. 111, p. 544 (1962)], where it was found to cause a 53% inhibition in swelling at the 33 mg./kg. dose level when given by the oral route. N-(2-Pyridyl)-2-methyl-4-(n-butyryloxy)-2H-1,2-benzothiazine-3-carboxamide 1,1-dioxide has been found to exhibit its therapeutic effect in rats when tested orally at levels ranging from 0.33-33 mg./kg., even retaining anti-inflammatory activity in adrenalectomized animals to a significantly high degree.

Furthermore, the blood levels obtained after topical administration of the herein described benzothiazine dioxide acyl derivatives are truly remarkable. For instance, N-(2-pyridyl)-2-methyl-4-(n-butyryloxy)-2H-1,2-benzothiazine-3-carboxamide 1,1-dioxide was found to elicit piroxicam blood levels in dogs as high as 0.11 $\mu$g./ml. after 48 hours when administered in an ointment base at the 1% concentration level, whereas piroxicam itself when administered under the same conditions at a higher concentration of 5% produced blood levels no higher than 0.05 $\mu$g./ml. over a 72-hour period.

The herein described N-(2-pyridyl)-2-methyl-4-acyloxy-2H-1,2-benzothiazine-3-carboxamide 1,1-dioxide anti-inflammatory agents can be administered via either the oral, parenteral or topical routes. In general, these compounds are most desirably administered in doses ranging from about 10 mg. up to about 1000 mg. per day, although variations will necessarily occur depending upon the weight and condition of the subject being treated and the particular route of administration chosen. However, a dosage level that is in the range of from about 0.16 mg. to about 16 mg. per kg. of body weight per day is most desirably employed. Nevertheless, variations may occur depending upon the species of animal being treated and its inividual response to said medicament, as well as on the type of pharmaceutical formulation and the time period and interval at which such administration is carried out. In some instances, dosage level below the lower limit of the aforesaid range may be more than adequate, while in other cases still larger doses may be employed without harmful side effects provided that such higher dose levels are first divided into several smaller doses for administration throughout the day.

The N-(2-pyridyl)-2-methyl-4-acyloxy-2H-1,2-benzothiazine-3-carboxamide 1,1-dioxide compounds of this invention may be administered alone or in combination with pharmaceutically acceptable carriers by either of the three routes previously indicated. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 0.5% to about 90% by weight.

For oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium sterarate, sodium lauryl sulfate and talc are often very useful for tabletting purposes. Solid compositions of a similar type may also be employed as fillers in gelatin capsules; preferred materials also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these N-(2-pyridyl)-2-methyl-4-acyloxy-2H-1,2-benzothiazine-3-carboxamide 1,1-dioxide derivatives in either sesame or peanut oil or in aqueous propylene glycol may be employed. The aqueous solutions should be suitably buffered if necessary and the liquid diluent first rendered isotonic with sufficient saline or glucose. These solutions are suitable for intravenous, intramuscular and subcutaneous injection purposes. Additionally, it is also possible to administer the aforesaid N-(2-pyridyl)-2-methyl-4-acyloxy-2H-1,2-benzothiazine-3-carboxamide 1,1-dioxide compounds topically when treating inflammatory conditions of the skin and this may be preferably done by way of creams, jellies, pastes, ointments and the like, in accordance with standard pharmaceutical practice.

The activity of the compounds of the present invention, as anti-inflammatory agents, is best determined by employing the previously mentioned standard carrageenin-induced rat foot edema test according to the general procedure described by C. A. Winter et al., as earlier reported in the *Proceedings of the Society of Experimental Biology and Medicine*, Vol. 111, p. 544 (1962). In this test, anti-inflammatory activity is determined as the percent inhibition of edema formation in the hind paw of male albino rats (weighing 150–190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed three hours after the carrageenin injection by measuring the volume of the injected paw initially as well as at the three-hour mark. The increase in volume three hours after carrageenin injection constitutes the individual response. Compounds are considered active if the difference response between the drug-treated animals (six rats/group) and the control group (i.e., animals receiving the vehicle alone) is significant on comparison with the results afforded by standard compounds like acetylsalicyclic acid at 100 mg./kg. or phenylbutazone at 33 mg./kg., both by the oral route of administration.

EXAMPLE 1

A mixture consisting of 1.66 g. (0.005 mole) of N-(2-pyridyl)-2-methyl-4-hydroxy-2H-1,2-benzothiazine-3-carboxamide 1,1-dioxide(piroxicam) suspended in 5 ml. of pyridine and 3 ml. of acetic anhydride was heated on a steam bath until solution was effected. The resulting yellow solution was then further heated in this manner for a period of one-half hour and finally, allowed to cool to room temperature ($\sim 25°$ C.). Upon concentration of the resulting reaction mixture to a low volume while under reduced pressure, there was ultimately obtained (after long standing) a yellow precipitate as the desired product. The latter material was subsequently recovered by means of suction filtration, washed well with diethyl ether and vacuum dried to afford 220 mg. (12%) of pure N-(2-pyridyl)-2-methyl-4-acetoxy-2H-1,2-benzothiazine-3-carboxamide 1,1-dioxide, m.p. 280°–282° C. The pure product was further characterized by means of mass spectroscopy and infrared absorption spectra. A negative reaction with ferric chloride reagent indicated the absence of the 4-hydroxy functionality.

EXAMPLE 2

In a dry three-necked round-bottomed flask containing 25 ml. of methylene chloride under a dry nitrogen atmosphere at 0° C., there was placed 4.0 g. (0.01208 mole) of N-(2-pyridyl)-2-methyl-4-hydroxy-2H-1,2-benzothiazine-3-carboxamide 1,1-dioxide and 1.22 g. (0.01208 mole) of triethylamine (1.7 ml.), followed by the slow careful addition of 1.54 g. (0.0145 mole) of n-butyryl chloride (1.5 ml.) thereto. The resulting slurry was then stirred in the cold ($\sim 0°$ C.) for approximately 15 minutes and then allowed to warm to room temperature ($\sim 25°$ C.) and stirred at that temperature for approximately 16 hours (i.e., overnight). The spent reaction mixture was then cooled in an ice bath and filtered while cold to remove as much triethylamine hydrochloride from the mixture as possible. The resulting mixture (as the filtrate) was then concentrated in vacuo to a foamy oil, which was subsequently redissolved in fresh methylene chloride and treated with two-fresh 25 ml. portions of water (as a wash). The organic phase which separated was then dried over anhydrous magnesium sulfate and filtered, followed by concentration in vacuo once again to give a thick, clear yellow oil.

The above oil was then taken up in 100 ml. of ethyl acetate and washed twice with separate 50 ml.—portions of saturated aqueous sodium bicarbonate. The separated organic phase was then backwashed with 50 ml. of water and dried over anhydrous sodium sulfate, followed by filtration and concentration to a thick oil. The latter oil was then placed under a high vacuum to yield a foam, which was subsequently taken up in a minimal amount of ethyl acetate ($\sim 15$ ml.) to afford a solution. Cooling and scratching of the latter solution ultimately gave a white crystalline solid, which was later collected by suction filtration, washed with a small amount of diethyl ether and dried in a desiccator. In this way, there was finally obtained 1.1 g. (23%) of pure N-(2-pyridyl)-2-methyl-4-(n-butyryloxy)-2H-1,2-benzothiazine-3-carboxamide 1,1-dioxide, m.p. 111°–113° C. The pure product was further characterized by means of mass spectroscopy and elemental analysis.

Anal. Calcd. for $C_{19}H_{19}N_3O_5S$: C, 56.85; H, 4.77; N, 10.47. Found: C, 56.27; H, 4.82; N, 10.43.

EXAMPLE 3

In a 75 ml. three-necked round-bottomed flask equipped with magnetic stirrer, dropping funnel and nitrogen-inlet tube, there were placed 2.0 g. (0.0060 mole) of N-(2-pyridyl)-2-methyl-4-hydroxy-2H-1,2-benzothiazine-3-carboxamide 1,1-dioxide and 25 ml. of methylene chloride while under a nitrogen atmosphere. Stirring was commenced and a yellow solution soon formed, to which 0.842 ml. (0.0060 mole) of triethylamine was rapidly added. The latter solution was then cooled in an ice bath, while a solution consisting of 0.848 ml. (0.00724 mole) of benzoyl chloride dissolved in 10 ml. of methylene chloride was slowly added from the dropping funnel in a dropwise manner over a period of five minutes. The resulting reaction mixture was then allowed to stir at ambient temperatures for a period of four hours. At the end of this time, the spent reaction mixture was treated with 20 ml. of water and the pH of the aqueous layer adjusted to a pH of 8 with the aid of sodium bicarbonate. The organic layer which separated at this point was removed and dried over anhydrous magnesium sulfate. Evaporation of the resulting filtrate while under reduced pressure then gave a white foam, which was subsequently treated with 10 ml. of ethyl acetate and slurried for five minutes. A white solid precipitate soon crystallized out. This latter material was then recovered by means of suction filtration and washed well with ethyl acetate to ultimately afford pure N-(2-pyridyl)-2-methyl-4-benzoyloxy-2H-1,2-benzothiazine-3-carboxamide 1,1-dioxide (m.p. 145°–148° C.) in a 508 mg. (19.5%) yield. The pure product was further characterized by means of mass spectroscopy and infrared absorption data, in addition to elemental analysis.

Anal. Calcd. for $C_{22}H_{17}N_3O_5S \cdot H_2O$: C, 58.27; H, 4.19; N, 9.26. Found: C, 58.02; H, 4.18; N, 9.01. A second crystalline crop (477 mg.) was subsequently recovered from the mother liquor. It melted at 153°–154° C. and proved to be identical in every respect with the original product.

EXAMPLE 4

In a 75 ml. three-necked round-bottomed flask equipped with magnetic stirrer, dropping funnel and nitrogen-inlet tube, there were placed 2.0 g. (0.0060 mole) of N-(2-pyridyl)-2-methyl-4-hydroxy-2H-1,2-benzothiazone-3-carboxamide 1,1-dioxide, 30 ml. of methylene chloride and 0.842 ml. (0.0060 mole) of triethylamine (all while under a nitrogen atmosphere). Stirring was commenced and a yellow solution soon formed. The solution was then cooled in an ice bath, while a solution consisting of 0.564 ml. (0.0072 mole) of methanesulfonyl chloride (mesyl chloride) dissolved in 10 ml. of methylene chloride was slowly added from the dropping funnel in a dropwise manner over a period of five minutes. At the end of this time, a heavy white precipitate formed and the resulting suspension was stirred at room temperature (~25° C.) overnight for a period of approximately 16 hours. The spent reaction mixture was then treated with 50 ml. of methylene chloride (with stirring) to form a yellow solution, followed by the addition of 50 ml. of water and further stirring for a period of five minutes. The pH of the aqueous phase, which was now pH 2, was subsequently readjusted to a pH value of 12 with the aid of added sodium bicarbonate solution. The separated organic layer was then dried over anhydrous magnesium sulfate and filtered, and the clear filtrate subsequently concentrated in vacuo to afford a yellow solid that was thereafter slurried with 50 ml. of ethyl acetate. The latter product was subsequently recovered by means of suction filtration and air dried to ultimately yield 2.02 g. (81%) of pure N-(2-pyridyl)-2-methyl-4-methanesulfonyloxy-2H-1,2-benzothiazine-3-carboxamide 1,1-dioxide, m.p. 175°–178° C. The pure product was further characterized by means of mass spectroscopy and infrared absorption spectra, in addition to elemental analysis.

Anal. Calcd. for $C_{16}H_{15}N_3O_6S_2$: C, 46.93; H, 3.69; N, 10.26. Found: C, 47.07; H, 3.93; N, 10.17.

EXAMPLE 5

In a 250 ml. three-necked round-bottomed flask equipped with magnetic stirrer, dropping funnel and nitrogen-inlet tube, there were placed 3.0 g. (0.0086 mole) of N-(6-methyl-2-pyridyl)-2-methyl-4-hydroxy-2H-1,2-benzothiazine-3-carboxamide 1,1-dioxide, 125 ml. of methylene chloride and 1.2 ml. (0.0086 mole) of triethylamine while under a dry nitrogen atmosphere. Stirring was then commenced and the latter solution was cooled in an ice bath, while a solution consisting of 0.743 ml. (0.010 mole) of acetyl chloride dissolved in 30 ml. of methylene chloride was slowly added from the dropping funnel in a dropwise manner over a period of five minutes. The resulting reaction mixture was then allowed to stir at ambient temperatures for a period of approximately 16 hours (i.e., overnight). At the end of this time, the spent reaction mixture was treated with 30 ml. of water and the pH of the aqueous layer adjusted to a pH of 10 with the aid of sodium bicarbonate. The organic layer which separated at this point was removed and subsequently dried over anhydrous magnesium sulfate. Evaporation of the resulting filtrate to near dryness while under reduced pressure then gave a yellow gum, which was subsequently dissolved in 10 ml. of ethyl acetate and stirred for a period of ten minutes. A yellow solid precipitate soon crystallized out. This latter material was subsequently recovered by means of suction filtration and washed well with ethyl acetate and ultimately afford 1.12 g. (34%) of pure N-(6-methyl-2-pyridyl)-2-methyl-4-acetoxy-2H-1,2-benzothiazine-3-carboxamide 1,1-dioxide, m.p. 159°–162° C. The pure product was further characterized by means of mass spectroscopy, thin layer chromatography acid and infrared absorption spectra, in addition to elemental analysis.

Anal. Calcd. for $C_{18}H_{17}N_3O_5S$: C, 55.80; H, 4.42; N, 10.84. Found: C, 55.50; H, 4.49; N, 10.95.

EXAMPLE 6

In a 250 ml. three-necked round-bottomed flask equipped with magnetic stirrer, dropping funnel and nitrogen-inlet tube, there was placed 3.5 g. (0.01013 mole) of N-(6-methyl-2-pyridyl)-2-methyl-4-hydroxy-2H-1,2-benzothiazine-3-carboxamide 1,1-dioxide and 50 ml. of methylene chloride while under a nitrogen atmosphere. Stirring was commenced and to the resulting organic suspension, there were added 1.4 ml. (0.0101 mole) of triethylamine. The yellow solution so obtained was then cooled in an ice bath, while a solution consisting of 1.4 ml. (0.0121 mole) of benzoyl chloride dissolved in 10 ml. of methylene chloride was slowly added from the dropping funnel in a dropwise manner over a period of ten minutes. The resulting reaction mixture as then allowed to stir at room temperature (~25° C.) for a period of approximately 64 hours (i.e., over the week-end). At the end of this time, the spent reaction mixture was treated with 50 ml. of water and the pH of the aqueous acidic layer was adjusted to a pH of 12 with the aid of sodium bicarbonate. The organic layer which separated at this point was removed and subsequently dried over anhydrous magnesium sulfate. Evaporation of the resulting filtrate to near dryness while under reduced pressure then gave a yellow gum, which was subsequently slurried with 30 ml. of ethyl acetate. A yellow solid material soon crystallized from the organic solution and was recovered by suction filtration. After washing the latter material with a small amount of ethyl acetate, the resulting white solid product was air dried to ultimately afford 2.09 g. (46%) of pure N-(6-methyl-2-pyridyl)-2-methyl-4-benzoyloxy-2H-1,2-benzothiazine-3-carboxamide 1,1-dioxide, m.p. 162°–164° C. The pure product was further characterized by means of mass spectroscopy, thin layer chromatography and infrared absorption spectra, in addition to elemental analysis.

Anal. Calcd. for $C_{23}H_{19}N_3O_5S$: C, 61.45; H, 4.26; N, 9.34. Found: C, 61.10; H, 4.62; N 9.30.

EXAMPLE 7

In a 250 ml. three-necked round-bottomed flask equipped with magnetic stirrer, dropping funnel and nitrogen-inlet tube, there were placed 3.0 g. (0.00868 mole) of N-(6-methyl-2-pyridyl)-2-methyl-4-hydroxy-2H-1,2-benzothiazine-3-carboxamide 1,1-dioxide, 100 ml. of methylene chloride and 1.2 ml. (0.00868 mole) of triethylamine while under a nitrogen atmosphere. Stirring was commenced and a yellow solution soon formed. The solution was then cooled in an ice bath, while a solution consisting of 0.812 ml. (0.0104 mole) of methanesulfonyl chloride (mesyl chloride) dissolved in 10 ml. of methylene chloride was slowly added from the dropping funnel in a dropwise manner over a period of five minutes. The resulting reaction mixture (a yellow solution) was then allowed to stir at ambient temperatures for a period of approximately 16 hours (i.e., overnight). At the end of this time, the spent reaction mixture was treated with 30 ml. of water and the pH of the aqueous acidic layer was adjusted to a ph of 10 with the aid of sodium bicarbonate. The organic layer which separated at this point was removed and subsequently dried over anhydrous magnesium sulfate. Evaporation of the resulting filtrate to near dryness while under reduced pressure then gave a yellow gum, which was subsequently slurried with 30 ml. of ethyl acetate for a period of 20 minutes. A pale yellow solid material was next removed from the organic mixture by means of suction filtration and air dried to finally give 1.57 g. (44%) of pure N-(6-methyl-2-pyridyl)-2-methyl-4-methanesulfonyloxy-2H-1,2-benzothiazine-3-carboxamide 1,1-dioxide, m.p. 189°–191° C. The pure product was further characterized by means of mass spectroscopy and infrared absorption spectra, in addition to elemental analysis.

Anal. Calcd. for $C_{17}H_{17}N_3O_6S_2$: C, 48.22; H, 4.04; N, 9.92 Found: C, 48.73, H, 4.11; N, 10.09.

EXAMPLE 8

The following acyl derivatives of N-(2-pyridyl)-2-methyl-4-hydroxy-2H-1,2-benzothiazine-3-carboxamide 1,1-dioxide and N-(6-methyl-2-pyridyl)-4-hydroxy-2H-1,2-benzothiazine-3-carboxamide 1,1-dioxide are respectively prepared by employing the procedures described in the previous Examples, starting from the appropriate 4-hydroxy compound in each instance:

N-(2-pyridyl)-2-methyl-4-(n-caproyloxy)-2H-1,2-benzothiazine-3-carboxamide 1,1-dioxide N-(2-pyridyl)-2-methyl-4-(n-nonyloxy)-2H-1,2-benzothiazine-3-carboxamide 1,1-dioxide N-(6-methyl-2-pyridyl)-2-methyl-4-(n-butyryloxy)-2H-1,2-benzothiazine-3-carboxamide 1,1-dioxide N-(6-methyl-2-pyridyl)-2-methyl-4-(n-nonyloxyl)-2H-1,2-benzothiazine-3-carboxamide 1,1-dioxide N-(2-pyridyl)-2-methyl-4-ethanesulfonyloxy-2H-1,2-benzothiazine-3-carboxamide 1,1-dioxide N-(2-pyridyl)-2-methyl-4-(n-butanesulfonyloxy)-2H-1,2-benzothiazine-3-carboxamide 1,1-dioxide N-(2-pyridyl)-2-methyl-4-(n-hexanesulfonyloxy)-2H-1,2-benzothiazine-3-carboxamide 1,1-dioxide N-(6-methyl-2-pyridyl)-2-methyl-4-(n-propanesulfonyloxy)-2H-1,2-benzothiazine-3-carboxamide 1,1-dioxide N-(6-methyl-2-pyridyl)-2-methyl-4-(n-hexanesulfonyloxy)-2H-1,2-benzothiazine-3-carboxamide 1,1-dioxide

EXAMPLE 9

A pharmaceutical composition in ointment form was prepared by blending the following ingredients together in the proportions by weight indicated below in the manner hereinafter indicated:

| | |
|---|---|
| N-(2-Pyridyl)-2-methyl-4-(n-butyryloxy)-2H-1,2-benzothiazine-3-carboxamide 1,1-dioxide | 1.0 |
| Lecithin | 0.8 |
| Sorbitan trioleate | 0.1 |
| Amerlate P[1] | 53.0 |
| Amerchol L500[2] | 35.0 |
| Beeswax | 10.0 |

[1] Amerlate P is the registered trademark name of American Cholesterol Products, Inc. of Edison, New Jersey for a sterol emulsifier-emollient-penetrant product consisting essentially of the isopropyl ester of normal, branched-chain and hydroxy acids of lanolin.

[2] Amerchol L500 is the registered trademark name of American Cholesterol Products, Inc. of Edison, New Jersey for a sterol emulsifier-emollient-penetrant product consisting essentially of a mixture of concentrated multisterol extract containing a selected fraction of lanolin sterols and higher alcohols.

All the ingredients in the above ointment base (i.e., the above combination of pharmaceutical carriers minus the essential active ingredient) were first melted together at a temperature below 90° C. and then cooled down slowly to room temperature (~25° C.) before being combined with N-(2-pyridyl)-2-methyl-4-(n-butyryloxy)-2H-1,2-benzothiazine-3-carboxamide 1,1-dioxide (the essential active ingredient), followed by further warming and stirring of the combined mixture at about 50°–60° C. While under a dry nitrogen atmosphere. After cooling to room temperature, the solidified ointment so obtained was then found to be suitable for topical administration to animals. When this ointment (which contained the essential active ingredient at the 1.0% concentration level) was applied directly to the skin of dogs, it was found to elicit blood levels of N-(2-pyridyl)-2-methyl-4-hydroxy-2H-1,2-benzothiazine-3-carboxamide 1,1-dioxide (i.e., piroxicam) as high as 0.11 μg./ml. at 48 hours post-dose, whereas piroxicam itself in the same ointment base at the 5% concentration level produced no blood levels greater than 0.05 μg./ml. over a 72-hour period.

EXAMPLE 10

A dry solid pharmaceutical composition is prepared by blending the following materials together in the proportions by weight specified below:

| | |
|---|---|
| N-(2-Pyridyl)-2-methyl-4-(n-butyryloxy)-2H-1,2-benzothiazine-3-carboxamide 1,1-dioxide | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 100 mg. of the active ingredient. Other tablets are also prepared in a similar fashion containing 5, 10, 25 and 50 mg. of the active ingredient, respectively, by merely using the appropriate amount of the N-(2-pyridyl)-2-methyl-4-acyloxy-2H-1,2-benzothiazine-3-carboxamide 1,1-dioxide derivative in each case.

EXAMPLE 11

A dry solid pharmaceutical composition is prepared by combining the following materials together in the proportions by weight indicated below:

| | |
|---|---|
| N-(2-Pyridyl)-2-methyl-4-methanesulfonyloxy-2H-1,2-benzothiazine-3-carboxamide 1,1-dioxide | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing the pharmaceutical composition are then prepared employing a sufficient quantity of material in each instance so as to provide each capsule with 250 mg. of the active ingredient.

EXAMPLE 12

An aqueous propylene glycol solution containing N-(2-pyridyl)-2-methyl-4-acetoxy-2H-1,2-benzothiazine-3-carboxamide 1,1-dioxide is prepared by dissolving the latter compound in propylene glycol-water (1:3 by weight) with the aid of gentle heating. The amount of compound employed is such that the resulting solution contains 5 mg. of the active ingredient per ml. of solution. After cooling to room temperature, it is sterilized by means of filtration through a Seitz filter. The sterile aqueous propylene glycol solution so obtained is then suitable for intramuscular administration to animals.

What is claimed is:

1. A compound of the formula:

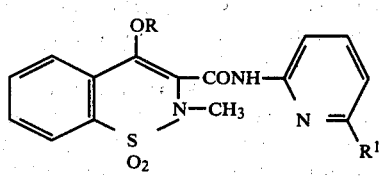

wherein R is selected from the group consisting of alkanoyl having from two to nine carbon atoms, benzoyl, toluoyl, thenoyl, furoyl, lower alkanesulfonyl and benzenesulfonyl, and $R^1$ is hydrogen or methyl.

2. A compound as claimed in claim 1 wherein R is alkanoyl and $R^1$ is hydrogen.

3. A compound as claimed in claim 1 wherein R is alkanoyl and $R^1$ is methyl.

4. A compound as claimed in claim 1 wherein R is benzoyl and $R^1$ is hydrogen.

5. A compound as claimed in claim 1 wherein R is benzoyl and $R^1$ is methyl.

6. A compound as claimed in claim 1 wherein R is lower alkanesulfonyl and $R^1$ is hydrogen.

7. A compound as claimed in claim 1 wherein R is lower alkanesulfonyl and $R^1$ is methyl.

8. N-(2-Pyridyl)-2-methyl-4-acetoxy-2H-1,2-benzothiazine-3-carboxamide 1,1-dioxide.

9. N-(2-Pyridyl)-2-methyl-4-(n-butyryloxy)-2H-1,2-benzothiazine-3-carboxamide 1,1-dioxide.

10. N-(6-Methyl-2-pyridyl)-2-methyl-4-acetoxy-2H-1,2-benzothiazine-3-carboxamide 1,1-dioxide.

11. N-(2-Pyridyl)-2-methyl-4-methanesulfonyloxy-2H-1,2-benzothiazine-3-carboxamide 1,1-dioxide.

12. N-(6-Methyl-2-pyridyl)-2-methyl-4-methanesulfonyloxy-2H-1,2-benzothiazine-3-carboxamide 1,1-dioxide.

13. A method for treating inflammatory conditions in a warm-blooded animal, which comprises administering to said animal an effective anti-inflammatory amount of a compound as claimed in claim 1.

14. A pharmaceutical composition comprising a pharmaceutically acceptable carrier and an effective anti-inflammatory amount of a compound as claimed in claim 1.

* * * * *